Feb. 23, 1943. R. L. BYRUM Plant Pat. 566
ROSE PLANT
Filed Feb. 3, 1942
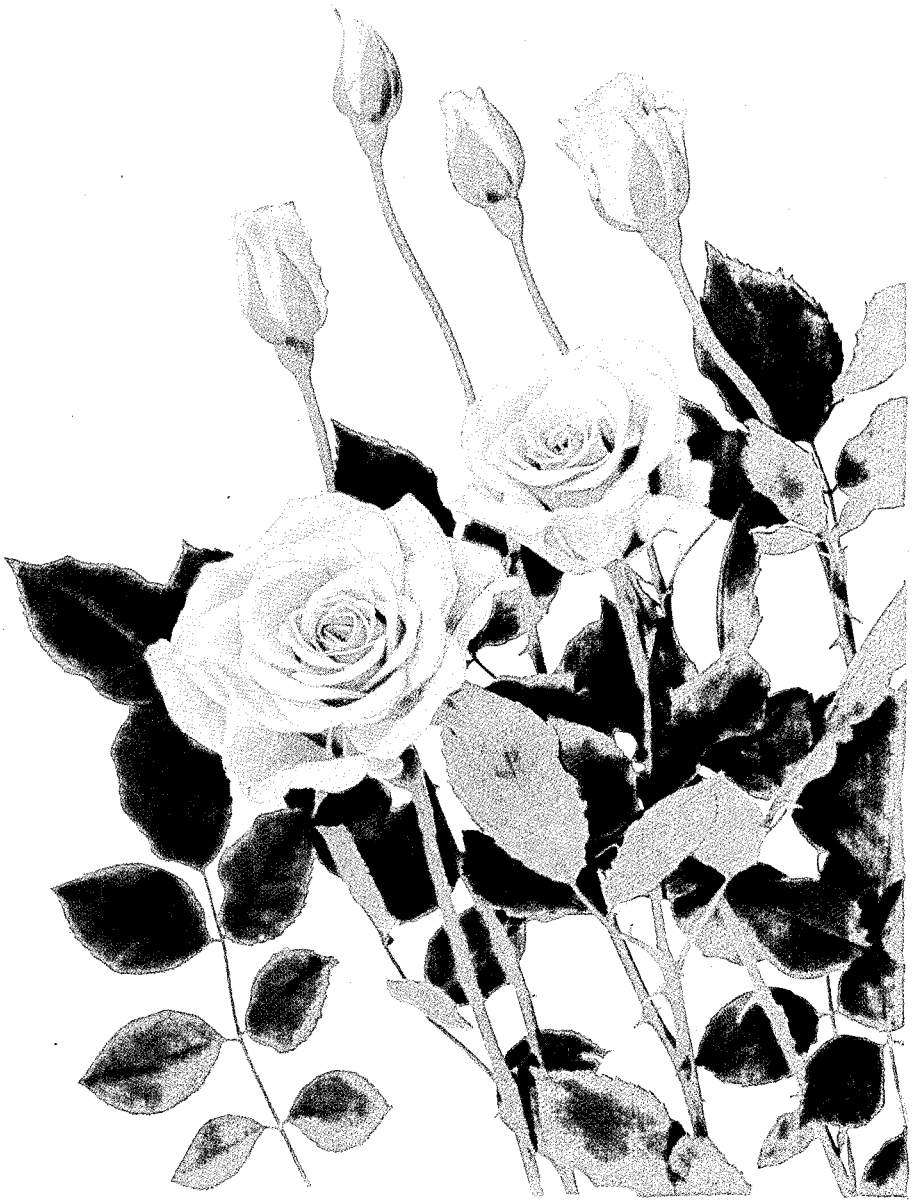
Inventor
Roy L. Byrum
By Robert Robb
Attorneys Patented Feb. 23, 1943

UNITED STATES PATENT OFFICE

566

ROSE PLANT

Roy L. Byrum, Richmond, Ind., assignor to Joseph H. Hill Company, Richmond, Ind., a corporation of Indiana Application February 3, 1942, Serial No. 429,433

1 Claim. (Cl. 47—61)

The present invention relates to a new and distinct variety of rose plant, originated by the crossing of varieties "Captain Glisson" and "R. M. S. Queen Mary," with the object in view of improving upon the growth characteristic of the latter variety.

This new variety has proved to be unlike any other greenhouse variety known to me and is characterized as to novelty: first, in respect to the superior ability of its blooms to attain and retain a deep, intense color as the flower opens than found in any other variety now available or known to me, the texture of the petals of said blooms being very thick and leathery from tight bud to wide open bloom and making the most desirable exhibition of petal texture within my knowledge; secondly, as to foliage in that it is medium size, heavy, of leathery texture, standing out stiffly from stem and very disease resistant; and thirdly, as to growth in that it is very upright yet much branched and the wood of the stems and branches, while not heavy, is very firm.

These primary features distinguish this new variety in characteristics important for functioning as a greenhouse type for cut flowers, and other equally desirable distinctions are set forth in the following detail description, in which color terminology relating to the flowers accords with Ridgway's Color Standard and general dictionary meaning.

Type: Half hardy; tall; bush; greenhouse; seedling; for cut flowers.

Class: Hybrid tea.

Parentage: Seedling.

*Seed parent.*—"Captain Glisson," Plant Patent No. 155.

*Pollen parent.*—"R. M. S. Queen Mary," Plant Patent No. 249.

Propagation: The distinguishing characteristics have been found to come true to form by the following methods of reproduction which are the only ones tried: by cuttings, grafting and budding.

*Flower*

Locality where grown: Richmond, Indiana.

Flowers borne: Singly to stem; in irregular cluster; on strong, medium length stems.

Quantity of bloom: Abundant in greenhouse.

Continuity: Continuous.

Fragrance: Slight tea.

Bud:

*Peduncle.*—Medium length; heavy; erect; stiff; light yellowish green; smooth; numerous light green prickles.

*Before calyx breaks.*—*Size*—small. *Form*—short, globular with a conspicuous neck; with foliaceous appendages on the surface of the bud; with stout, much cut, bristle-like foliaceous parts extending beyond the tip of the bud equal to three-fourths or more of its length.

*As calyx breaks.*—*Color*—Coral Red, Plate XIII.

*As first petal opens.*—*Size*—small. *Form*—short: globular, end of bud being flat. *Color*—outside, base—Pale Lemon Yellow, Plate IV, shading to Light Coral Red, Plate XIII, at end of petal. Inside, base—Empire Yellow, Plate IV, shading to Coral Pink, Plate XIII, penciled with streaks of Coral Red, Plate XIII. *Opening*—opens up well.

Bloom:

*Size, when fully open.*—Medium; 3½ inches to 4 inches.

*Petalage.*—Double; from thirty to thirty-five petals arranged irregularly.

*Form.*—Very full; globular at first, becoming open; petals remaining at first tightly rolled outward, becoming later, at maturity, loosely rolled outward.

Petals: Thick; leathery; with inside satiny and outside shiny, satiny.

*Shape.*—Outside, obovate; scalloped with one notch; intermediate, obovate; scalloped with one notch; inside—obovate; scalloped irregular with one notch.

This description of a newly opened flower was made from a rose grown in a greenhouse, in the month of October, 1941, at Richmond, Indiana:

*Color*: Outside petal: outside surface, base—Pale Lemon Yellow, Plate IV, changing to Coral Pink, Plate XIII, at end of petals; inside surface, base—Empire Yellow, Plate IV, changing to Venetian Pink, Plate XIII, penciled with streaks of Coral Pink, Plate XIII. Intermediate petal: outside surface, base—Pale Lemon Yellow, Plate IV, shading through Coral Buff, Plate XIII, to Flesh Pink, Plate XIII; inside surface, base—Empire Yellow, Plate IV, changing to Flesh Pink, Plate XIII, penciled slightly with Coral Pink, Plate XIII. Inner petal: outside surface, base—Pale Lemon Yellow, Plate IV, changing to Coral Pink, Plate XIII; inside surface, base—Empire Yellow, Plate IV, changing to Coral Pink, Plate XIII.

This description was made from a rose that was open for three days, in a greenhouse, in the month of October, 1941, at Richmond, Indiana:

*Color.*—Outside petal: outside surface, base—Pale Lemon Yellow, Plate IV, changing to Rhodonite Pink, Plate XXXVIII, at end of petal; inside surface, base—Empire Yellow, Plate IV, changing to White with slight cast of Pale Rhodonite Pink, Plate XXXVIII. Inside petal: outside surface, base—Pale Lemon Yellow, Plate IV, changing to Rhodonite Pink, Plate XXXVIII; inside surface, base—Empire Yellow, Plate IV, changing to Pale Rhodonite Pink, Plate XXXVIII.

*General color effect.*—Newly opened flower—Light Salmon Orange, Plate II. Three days open—Safrano Pink, Plate II.

*Behavior.*—Persist.

*Flower longevity.*—As cut roses grown in greenhouse, kept at living room temperatures, five to six days in October, 1941.

*Reproductive organs*

Stamens: Many; arranged regularly about pistils
Filaments: Medium long; yellow reddish; most with anthers.
Anthers: Medium size; reddish; open at various times.
Pollen: Abundant; gold.
Pistils: Many.
Styles: Even; medium long; thin; bunched.
Stigma: White.
Ovaries: Some protruding from calyx.
Sepals: Permanent; moderately short; spear-shaped; curled.

*Color.*—Inside—Light Bice Green, Plate XVII, overlaid with white fuzz. Outside—Light Bice Green, Plate XVII.

*Plant*

Foliage:

*Leaves.*—Compound of five to seven leaflets; very abundant; medium large; heavy; leathery.

*Leaflets.*—Ovoid, with apex acute; base obtuse; margin simply serrate.

*Color.*—Mature: upper surface—normal dark green; under surface—light green. Young: upper surface—moderately light green; under surface—green bronze edges.

*Rachis.*—Heavy. Upper side—grooved, hairy. Under side—extremely smooth, prickly.

*Stipules.*—Very short; very narrow; with short points turning out at an angle of more than 45°.

*Disease.*—Resistant to mildew, blackspot.

Growth:

*Habit.*—Bush; upright; much branched.

*Growth.*—Free; vigorous.

*Canes.*—Medium heavy.

*Main stems.*—Dull bronze red. *Thorns*—many; long; hooked downward; with broad, round base. *Prickles*—none. *Hairs*—none.

*Branches.*—Bright green. *Thorns*—many; long; hooked downward; broad, round base. *Prickles*—none. *Hairs*—none.

*New shoots.*—Bronze red. *Thorns*—many; straight; round base. *Prickles*—none. *Hairs*—none.

I claim:

A new and distinct variety of rose plant, characterized as to novelty by its habit of very upright, much branched growth, firmness of wood of stems and branches; heavy, leathery texture of foliage growing out stiffly from stems and possessing high disease resistance; and novel color, petal texture and quality of its blooms, substantially as shown and described.

ROY L. BYRUM.